United States Patent
Linde et al.

(10) Patent No.: US 7,338,461 B2
(45) Date of Patent: Mar. 4, 2008

(54) MODIFIED ORGAN SUPPORT DEVICES

(75) Inventors: Peter G. Linde, Dedham, MA (US);
Winfred W. Williams, Milton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 11/050,398

(22) Filed: Feb. 2, 2005

(65) Prior Publication Data
US 2005/0182349 A1    Aug. 18, 2005

Related U.S. Application Data

(60) Provisional application No. 60/541,533, filed on Feb. 2, 2004.

(51) Int. Cl.
*A61M 37/00* (2006.01)
*A01N 1/00* (2006.01)
*C12M 1/42* (2006.01)
*B01D 11/00* (2006.01)

(52) U.S. Cl. .................. 604/5.01; 604/4.01; 435/1.1; 435/284.1; 210/645

(58) Field of Classification Search .............. 604/4.01, 604/6.01, 5.01–5.04, 6.09, 7, 6.06, 6.14, 604/6.16; 422/44–48; 128/898; 435/1.1, 435/818, 284.1, 289.1, 286.6, 290.1, 290.4, 435/297.1–297.2, 297.4; 210/645, 646, 600, 210/634, 641, 650, 651, 739, 741, 97, 134, 210/137, 141, 142, 194, 196, 195.1–195.3, 210/252, 254–5, 257.1–257.2, 258–260, 210/294, 295, 321.6, 322, 321.71–321.72, 210/902, 929
See application file for complete search history.

(56) References Cited

U.S. PATENT DOCUMENTS

| 4,675,002 | A | * | 6/1987 | Viles et al. ................ 604/6.06 |
| 4,885,087 | A | * | 12/1989 | Kopf ..................... 210/321.72 |
| 5,290,684 | A | | 3/1994 | Kelly |
| 5,368,555 | A | | 11/1994 | Sussman et al. |
| 5,643,794 | A | * | 7/1997 | Liu et al. ................ 435/289.1 |
| 5,976,870 | A | | 11/1999 | Park |
| 6,294,380 | B1 | | 9/2001 | Qiang et al. |
| 6,582,955 | B2 | | 6/2003 | Martinez et al. |
| 6,913,588 | B2 | * | 7/2005 | Weitzel et al. ............ 604/6.09 |
| 2003/0054544 | A1 | | 3/2003 | Gruenberg |
| 2003/0228685 | A1 | | 12/2003 | Nyberg |

OTHER PUBLICATIONS

Bolasco et al., "Convection versus diffusion in dialysis: an Italian prospective multicentre study," Nephrol. Dial. Transplant. 18 [Suppl 7]:vii50-vii54 (2003).
Borra et al., "Mixed predilution and postdilution online hemodiafiltration compared with the traditional infusion modes," Int. J. Artif. Organs. 25:939-949 (2002).
Pedrini et al., "Advanced technology for extracorporeal liver support system devices," Kid. Int. 58(5):2155-65 (2000).
"Deaths and Hospitalizations from Chronic Liver Disease and Cirrhosis—United States, 1980-1989," MMWR 41(52):969-973, Jan. 8, 1993 http://www.cdc.gov/mmwr/preview/mmwrhtml/00018761.htm.
Awad, S. et al., "Results of a Phase I Trial Evaluating a Liver Support Device Utilizing Albumin Dialysis," Surgery 120(2):354-362, Aug. 2001.

(Continued)

Primary Examiner—Patricia Bianco
(74) Attorney, Agent, or Firm—Fish & Richardson P.C.

(57) ABSTRACT

Methods and devices are provided that improve the function of organ support devices, and also provided are improved methods of treating conditions associated with hemodynamic instability.

26 Claims, 7 Drawing Sheets

OTHER PUBLICATIONS

De Vriese, A. et al., "Cytokine Removal during Continuous Hemofiltration in Septic Patients," J. Am. Soc. Nephrol, 10:846-853, 1999.

Detry, O. et al., "Clinical use of a bioartificial liver in the treatment of acetaminophen-induced fulminant hepatic failure," Am. Surg., 65(10):934-8, Oct. 1999.

Ellis, A. et al., "Pilot-Controlled Trial of the Extracorporeal Liver Assist Device in Acute Liver Failure," Hepatology, 24(6):1446-1451, 1996.

Ferenci, P. "Pathogenesis of Hepatic Encephalopathy," UpToDate, 2003 http://www.utdol.com/application/topic/print.asp?file=cirrhosi/7310&type=A&selectedTi...

Forsythe, S. and Schmidt, G., "Sodium Bicarbonate for the Treatment of Lactic Acidosis," CHEST, 117(1):260-267, Jan. 2000.

Kellum, J. et al., "Diffusive vs. convective therapy: Effects on Mediators of Inflammation in Patients with Severe Systemic Inflammatory Response Syndrome," Crit. Care Med., 26(12):1995-2000, Dec. 1998.

Kim, W. et al., "Burden of Liver Disease in the United States: Summary of a Workshop," Hepatology 36(1):227-242, Jul. 2002.

Kjaergard, L. et al., "Artificial and Bioartificial Support Systems for Acute and Acute-on-Chronic Liver Failure," JAMA, 239(2):217-222, Jan. 8, 2003.

Levraut, J. et al., "Effect of continuous venovenous hemofiltration with dialysis on lactate clearance in critically ill patients," Crit. Care Med., 25(1):58-62, Jan. 1997.

Maxvold, N. et al., "Amino acid loss and nitrogen balance in critically ill children with acute renal failure: A prospective comparison between classic hemofiltration and hemofiltration with dialysis," Crit. Care Med., 28(4):1161-1165, Apr. 2000.

Millis, J. et al., "Initial Experience with the Modified Extracorporeal Liver-Assist Device for Patients with Fulminant Hepatic Failure: System Modifications and Clinical Impact," Transplantation, 74(12):1735-1746, Dec. 27, 2002.

Mitzner, S. et al., "Extracoporeal Detoxification Using the Molecular Adsorbent Recirculating System for Critically Ill Patients with Liver Failure," J. Am. Soc. Nephrol., 12:S75-S82, 2001.

Patzer, J. et al., "Novel Bioartifical Liver Support System: Preclinical Evaluation," Annals New York Academy of Sciences, p. 340-352., 1999.

Patzer, J. et al., "Preclinical Evaluation of the Excorp Medical, Inc, Bioartificial Liver Support System," J. Am. Coll. Surg., 195(3):299-310, Sep. 2002.

Pazzi, P. et al., "Serum bile acids in patients with liver failure supported with a bioartificial liver," Alimentary Pharmacology & Therapeutics, 16(8):1547, Aug. 2002.

Sauer, I. et al., "Development of a Hybrid Liver Support System," Annals New York Academy of Sciences, p. 308-319, 2001.

Stevens, C. "Liver Support Systems," UpToDate, 2003, http://www.utdol.com/application/topic/print.asp?file=hep_dis/I6014&type=A&selectedTi..

Strain, A. and Neuberger, J., "A Bioartificial Liver—State of the Art," Science 295:1005-1009, Feb. 8, 2002.

* cited by examiner

MODIFIED ORGAN SUPPORT DEVICES

RELATED APPLICATIONS

This application claims priority from U.S. Provisional Application No. 60/541,533, filed Feb. 2, 2004, which is incorporated herein by reference in its entirety.

TECHNICAL FIELD

This invention relates to the field of extracorporeal blood treatment systems, such as bioartificial liver support devices.

BACKGROUND

A variety of conditions are characterized by an organism's inability to maintain the hemodynamic stability of its circulatory system. In many conditions, hemodynamic instability is associated with an organism's failure to perform one or more of the following normal functions: detoxify blood, metabolize products in the blood, synthesize products required for the maintenance of hemodynamic stability, and modulate factors from the hormone or immune systems. Prominent examples of conditions that result in hemodynamic instability include loss of organ function and sepsis.

Loss of organ function is a serious risk to survival of an organism. A number of approaches to compensate for the loss of organ function have been developed. The ability to compensate for loss of an organ's function varies with both the organ that fails and the type of organ failure. For example, loss of kidney function can be treated with extracorporeal blood treatments that involve passing a patient's blood through a hemodialysis device. The hemodialysis device purifies a patient's blood using a dialysate that promotes diffusion of toxins from the blood to the dialysate. In many cases hemodialysis treatment can continue for years after the patient has lost substantial kidney function.

Liver failure, on the other hand, has proven more difficult to treat. The mortality rate for acute hepatic failure remains alarmingly high (over 50%). No effective therapy has been developed for the treatment of acute liver failure, and survival is best ensured only after total liver replacement by transplantation. Although liver transplants have a good success rate for curing patients with liver failure, ~90%, transplantation is not a viable option for the majority of persons suffering from liver failure for several reasons. First, the high cost of liver transplants effectively places transplantation beyond the reach of many patients. Second, many patients forgo transplant procedures because of the widely recognized shortage of donor livers available for transplantation. In 2002, 5,329 liver transplant procedures were performed, despite the fact that over 17,000 people were on the United States' national waiting list for a donor liver. (Source: Organ Transplantation Network (OPTN) web site, Richmond, Va.). From Jan. 1, 1995 to Oct. 31, 2004, 15,281 persons died while on the waiting list for a donor liver, and an additional 4,009 patients were removed from the waiting list because they were "too sick" for a transplant operation.

SUMMARY

The invention is based, in part, on new designs for organ support devices and methods of using organ support devices. In some embodiments, the new devices include recirculation loops, hemodialysis devices, and differential fluid flow rates to improve the function of the organ support device. The use of recirculation loops, hemodialysis devices, and differential fluid flow rates significantly improves the ability of an organ support device to remove toxic substances, e.g., ammonia, lactic acid, and inflammatory cytokines, that accumulate in the blood of a patient being treated with an organ support device, while also maintaining the critical balance between blood withdrawn and blood returned to the patient. The recirculation loops improve bioartificial organ function, in part, by ensuring that at least some fraction of a patient's blood is exposed to the bioartificial organ multiple times, thus effectively increasing the amount of time a patient's blood fraction is in contact with the biological component of an organ support device.

Also described herein are methods of using higher than atmospheric concentrations of oxygen to significantly improve the function of the organ support device, e.g., by exposing bioreactor hepatocytes to higher than atmospheric concentrations of oxygen.

The new methods and devices improve organ assist devices for use in a variety of treatments including treatment of liver failure, acute pancreatitis, kidney failure, sepsis, autoimmune disorders, and treatment of other conditions associated with hemodynamic instability.

In general, new organ support systems are described that feature a hemodialysis device and a hemodialysis recirculation conduit. Hemodialysis devices include, but are not limited to devices with a continuous venovenous hemofiltration device. A hemodialysis recirculation conduit includes a first end and a second end, as well as an inlet and an outlet that are both located between the first end and the second end. The first end of the conduit is configured to connect to a port on the hemodialysis device, e.g., an inlet port. The second end of the conduit is configured to connect to a different port on the hemodialysis device, e.g., a dialyzed fluid output port. In some embodiments, a first line, e.g., an arterial line, can bring fluid, e.g., blood from a subject, to the inlet of the hemodialysis recirculation conduit; and a second line can carry dialyzed fluid from the outlet, e.g., to a subject. Generally, the system is configured so that at least a portion of the fluid, e.g., a subject's blood, that is brought to the inlet of the recirculation conduit can be dialyzed more than once by the hemodialysis device before the fluid is removed by the second line. Thus, in the new systems, at least a portion of a subject's blood can be dialyzed multiple times before the blood is removed from the recirculation conduit by the second line and carried to the subject.

In some embodiments, the organ support systems also include a bioreactor, for example, a bioartificial liver support bioreactor. The bioreactor is arranged within the system to receive at least a fraction of dialyzed fluid from the hemodialysis device and thereby generate processed fluid. In this system, at least a portion of processed fluid can be dialyzed and/or processed by the bioreactor multiple times. In certain embodiments, an organ support system further includes an ultrafiltrate (UF) generator arranged to receive fluid from the first line or from the hemodialysis device. The UF generator can separate the fluid it receives into an ultrafiltrate fraction and a concentrated fluid fraction. In some embodiments, where a UF generator is arranged to receive fluid from the first line, the generated ultrafiltrate fraction is subsequently passed to the hemodialysis to dialyze the ultrafiltrate fraction.

Alternatively, in other embodiments, the UF generator is arranged to receive dialyzed fluid from the hemodialysis device, and the system can thus separate dialyzed fluid into an ultrafiltrate and a concentrated fluid fraction. Ultrafiltrate can then be passed to the bioreactor to generate "processed ultrafiltrate fraction." In some embodiments, an organ support system is arranged so that the processed ultrafiltrate fraction can be recombined with the concentrated fluid fraction to thereby generate a processed whole fluid fraction. The processed whole fluid fraction can be subsequently divided into a first portion of processed whole fluid and a second portion processed whole fluid. The first portion of processed whole fluid can be recirculated to the hemodialysis device, and the second portion processed whole fluid can be removed from the recirculation conduit by the second line.

In another aspect, described herein are methods for enhancing the function of a bioartificial organ support system by recirculating a portion of a subject's blood through a hemodialysis device, e.g., a device that includes continuous venovenous hemofiltration device. Generally, at least a fraction of a subject's blood is passed through a hemodialysis device to produce dialyzed blood. Dialyzed blood is then separated into a first dialyzed portion and a second dialyzed portion. The first dialyzed portion is recirculated through the hemodialysis device; and the second dialyzed portion is returned to the subject.

In some embodiments, the methods include passing at least a fraction of the dialyzed portion of blood through a bioreactor, e.g, a bioartificial liver support bioreactor, to generate processed blood. The processed blood is then separated into a first processed portion and a second processed portion. The first processed portion is recirculated through the hemodialysis device and the bioreactor. The second processed portion is returned to the subject.

In other embodiments, dialyzed blood is passed to an ultrafiltrate generator to generate an ultrafiltrate fraction and a concentrated blood fraction. The ultrafiltrate fraction is then processed by the bioreactor to generate processed ultrafiltrate. Subsequently, processed ultrafiltrate is combined with the concentrated blood fraction to form processed whole blood. Processed whole blood can be separated into a first portion of processed whole blood and a second portion of processed whole blood. The first portion of processed whole blood is recirculated through the hemodialysis device and the bioreactor, and the second portion of processed whole blood is returned to the patient.

In yet another aspect, the invention features methods for enhancing the function of an organ support system described herein by adjusting the flow rates of fluids in the system. In these methods, a recirculated flow rate refers to a flow rate of the fluids that are recirculated through a hemodialysis recirculation conduit (or loop). The non-recirculated flow rate refers to flow rate of fluids that are not recirculated, e.g., the flow rate of fluid taken from or returned to a subject. Generally, the method comprises maintaining or adjusting these flow rates in the system until they achieve a steady state and the ratio of the recirculated flow rate to the non-recirculated flow rate is any ratio between 0.1 to 1 and 10 to 1, inclusive.

The invention also features methods for enhancing the function of a bioreactor, e.g., a bioartificial liver support bioreactor, in a bioartificial organ support system. Generally, the methods include exposing cells in the bioreactor to a higher than atmospheric concentration of oxygen, subsequently processing blood, or a blood fraction, in the bioreactor to produce processed blood, and delivering at least a portion of the processed blood to a subject. Higher than atmospheric concentrations of oxygen that can be used in this method generally include any concentration of oxygen is at least approximately 26% and less than 79%. In some embodiments, the higher than atmospheric concentration of oxygen is a concentration between approximately 26% and approximately 70%. In certain embodiments, the higher than atmospheric concentration of oxygen is approximately 52.6%, or approximately 26%, or approximately 65%.

In some embodiments, this higher concentration of oxygen can be achieved, for example, by adding a gas that includes oxygen to (i) the blood or blood fraction introduced to the bioreactor or (ii) to the bioreactor itself, e.g., by bubbling gas into a bioreactor. In some embodiments, a gas with oxygen is added to the bioreactor before a subject's blood or blood fraction is introduced to the bioreactor. In other embodiments, a gas that includes oxygen is added (to the bioreactor, blood or blood fraction) as the blood or blood fraction is introduced to the bioreactor.

In one example of the method, a gas that includes oxygen is added to the ultrafiltrate fraction of a subject's blood to thereby achieve a higher than atmospheric concentration of oxygen. The oxygenated ultrafiltrate is subsequently processed in the bioreactor. Optionally, the processed ultrafiltrate can then be mixed with the concentrated blood fraction to produce processed whole blood, prior to returning at least a portion of the processed whole blood to the patient.

As used herein, a "bioartificial organ support device" is a device that uses cultured organ cells to enhance, support, or replace normal organ function in a subject, such as an animal or human patient.

As used herein, a "bioreactor" is a component of a bioartificial organ support device that contains living cells, which are intended to enhance, support, or replace normal organ function in an organism.

"Hepatocytes," as used herein, include living cells appropriate for use in the bioreactor of a bioartificial liver support device, e.g., human liver cells, animal liver cells, and cell lines, derived from human and non-human hepatocyte sources.

As used herein, phrases that describe the movement of fluid to (a), from (b), or between (a) and (b), where (a) and (b) are elements of an organ support device, also describe the movement of fluid through one or more intervening elements. For example, the phrases "(a) is arranged to receive fluid from (b)" and "(a) is arranged to carry fluid from (b)" means that fluid can pass from (b) to (a) directly or that fluid can pass from (b), through intervening element (c), and then to (a). The phrase "fluid can pass to (b)," means that fluid can pass directly to (b) or also that fluid can pass through intervening element (c) before being passed to (b).

The phrase "(a) is connected (b)," means that (a) can be connected directly to (b), or that (a) can be connected to (b) through an intervening element (c).

As used herein, a subject is a human or a non-human animal, such as, a dog, cat, bird, monkey, goat, sheep, pig, cow, rat, mouse, or frog; and a subject is not a component of a hemodialysis recirculation loop or hemodialysis recirculation conduit.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

Like reference symbols in the various drawings indicate like elements. Arrows in all the drawings indicate the direction of fluid flow through the devices.

DETAILED DESCRIPTION

The new methods and systems are described herein in the content of a specific bioartificial liver support device. Nevertheless, it should be recognized that the methods and systems described in the present specification and the claims may also be used in conjunction with other bioartificial organ support devices.

Components of the Recirculation Devices

In one aspect, the present application discloses hemodialysis (HD) recirculation loops for use with artificial and bioartificial organ support devices and methods for using HD recirculation loops. By way of illustration, this disclosure refers to the use of these recirculation loops in conjunction with bioartificial liver support (BAL) devices such as the extracorporeal liver assist device (ELAD™), HepatAssist™, Berlin Extracorporeal Liver Support (BELS), and Bioartificial Liver Support System™ (BLSS) devices referred to below.

The HD recirculation loops, or HD recirculation conduits, can include multiple components such as multiple pieces of tubing, connectors, pumps, flow meters, and other components that are suitable for use with an extracorporeal blood treatment device. By way of example, the tubing, connectors, pumps, flow meters, etc. that are used to modify an ELAD™ device to include an HD recirculation loop can be the same as the tubing, connectors, pumps, flow meters, and other components that are used in an unmodified ELAD™ device, e.g., as described in U.S. Pat Nos. 6,561,997 and 5,368,555. The recirculation loops disclosed herein can also utilize materials and components that are appropriate for use with a BAL device, even if those materials and components are not presently used with a BAL device. For example, different types of tubing, connectors, flow meters, etc. could be used to build a BAL device, or replace the components of an existing BAL device. The materials and parts that are appropriate for use in a BAL device are also appropriate for use in the HD recirculation loops disclosed herein.

A Prior Art BAL Device

Figure 1:
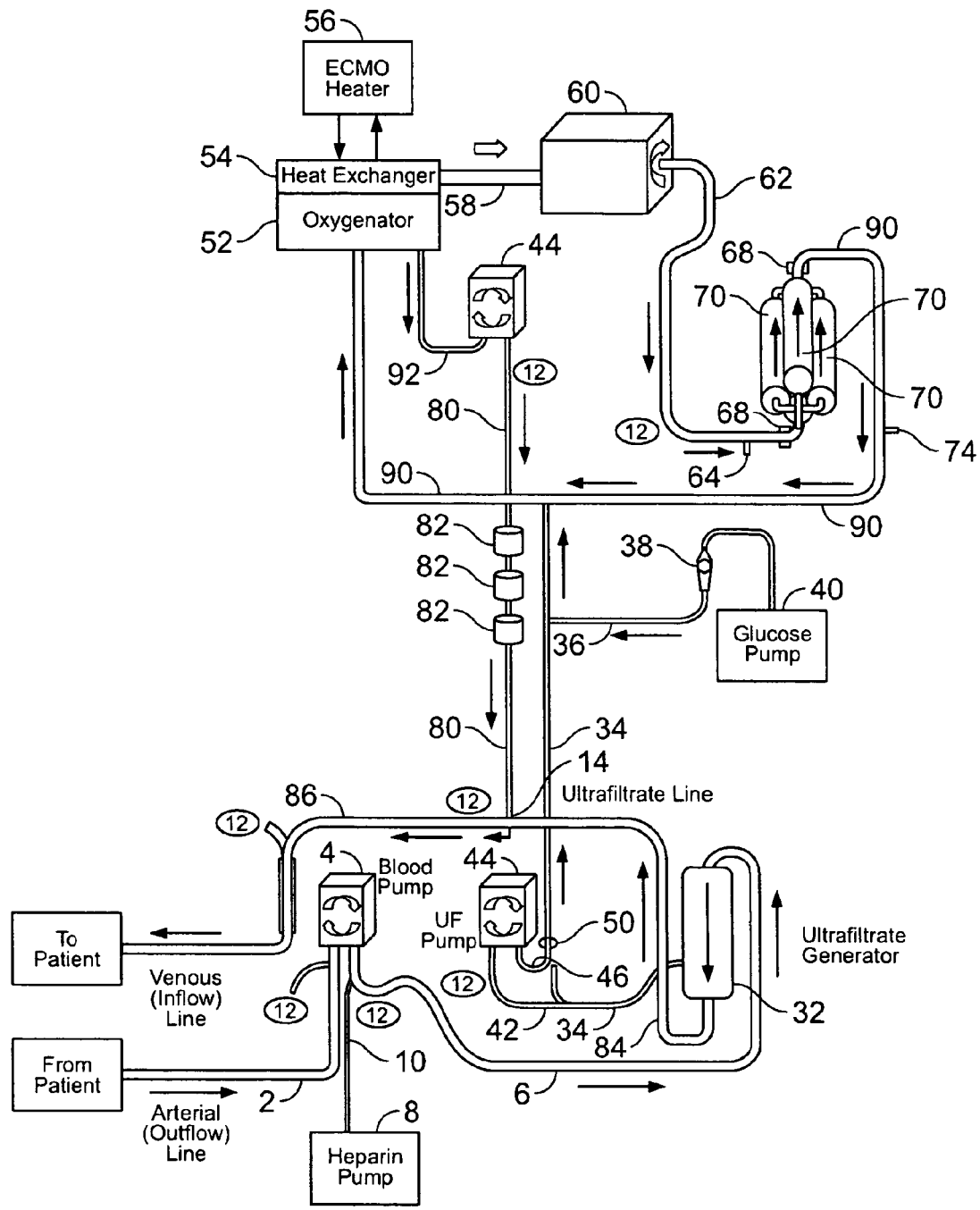
FIG. 1 is a schematic diagram of a prior art bioartificial liver support system, the ELAD™ (Vital Therapies, Inc., San Diego, Calif.) that does not include a hemodialysis recirculation loop.

FIG. 1 is a schematic view of the blood flow circuit through a prior art ELAD™ (Vital Therapies, Inc., San Diego, Calif.) device. An arterial line 2 withdraws blood from a patient through a double lumen venous catheter 1 (or any other suitable means of withdrawing blood from a patient's vein). The flow of blood through the arterial line is aided by a pump 4. A thinning agent such as heparin or citrate can be added to the blood, e.g. by a heparin pump 8 through line 10. Heparinized blood is carried by line 6 to an ultrafiltrate (UF) generator 32. The UF generator separates blood into a concentrated blood fraction, which is discharged into line 84, and an ultrafiltrate (UF) fraction which is discharged into the UF line 34. The flow of ultrafiltrate in line 34 is controlled by a UF pump 44 that draws UF from line 34 via line 42, and returns UF to the ultrafiltrate line 34 via line 46. Glucose is added to the UF line 34 from glucose pump 40 via a glucose infusion line 36. The flow of glucose into the line 34 can be controlled by a ratchet clamp 36.

Leaks along the UF line are monitored by blood leak detector 50. UF flows from line 34 into (e.g., via a T-connector or three-way stopcock) the post-ELAD™ recirculation line 90. UF then enters an oxygenator/warmer compartment 52. A heat exchanger 54 in the oxygenator/heater compartment is warmed by an external Extracorporeal Membrane Oxygenation (ECMO) heater 56. Warmed and oxygenated UF is passed through a line 58 to a centrifugal pump 60. It is worth noting, that in the current clinical setting, an ELAD™-treated patient's UF is typically oxygenated by a gas with atmospheric or ambient oxygen concentrations.

UF is discharged from the centrifugal pump to the ELAD™ cartridge UF inlet line 62, which includes a sampling port 64 that can be used to monitor the characteristics of Ultrafiltrate (UF) before it is exposed to hepatocytes in the ELAD™ hepatocyte cartridges 70. The ELAD™ cartridge inlet line 62 and the ELAD™ cartridge outlet line, i.e., the post-ELAD™ recirculation line 90, are connected to the ELAD™ cartridges 70 by quick disconnects 68.

UF from line 62 passes through the ELAD™ cartridges, which contain the BAL hepatocytes, 70 and is then discharged through the post-ELAD™ recirculation line 90, which includes a sampling port 74. UF which has been processed by the ELAD™ cartridges is mixed with unprocessed UF from line 34. This mixture of processed and unprocessed UF (processed UF mixture) is taken along line 90 to the oxygenator 54. A portion of the processed UF mixture is drawn from the oxygenator through line 92, using a UF pump 44, and discharged into the UF filter line 80. UF in line 80 is passed through an in-line series of cell filters 82. The processed UF mixture is then mixed with the concentrated blood fraction discharged from the UF generator 32 into the concentrated blood fraction line 84. The concentrated blood fraction from the UF generator is carried by the concentrated blood fraction line 84 to a T-connector or three-way stopcock 14. The T-connector or three-way stopcock mixes concentrated blood from line 84 and the processed UF from line 80 to form processed whole blood which is carried by line 86 back to the patient. Pumps 12 distributed at different points in the ELAD™ system maintain fluid flow throughout the system.

The diagram does not show a control console that can be used to digitally control pumps and monitor blood flow throughout the system. The control console, as well as some of the other device elements described above can be devices adapted from a heart lung machine platform, such as a Terumo® cardiovascular system (Terumo Cardiovascular Systems Corp., Ann Arbor, Mich.). Additional details describing the ELAD™ device and its use in the clinical setting are found in U.S. Pat. No 5,368,555 and in Millis et al., Transplantation 74: 1735-46 (2002).

Current BAL Treatments

Known BAL devices can develop a build-up of free ammonia in the BAL circuit. Fixing free ammonia into urea is an important function of normal liver cells. Another function that metabolically active liver cells provide is the consumption of amino acids such as glutamine and alanine that can contribute to a patient's overall ammonia load. It is not surprising, then, that patients suffering from liver failure should also suffer a sharply diminished capacity to down-regulate levels of free ammonia in their blood stream. This issue has not been satisfactorily addressed by existing BAL devices for two reasons. First, currently available bioartificial liver devices are incapable of fully compensating for the liver's normal ammonia regulating functions. Second, the problem may be compounded by the documented observation that some bioartificial liver devices actually produce free ammonia. Free ammonia build-up is a serious concern because high ammonia levels may be responsible for such unwanted side effects as the development of cerebral edema and hepatic encephalopathies in patients undergoing treatment with a BAL device.

A second issue associated with the use of current BAL devices is the build-up of lactic acid in the BAL circuit. Lactic acid build-up in patients being treated with a BAL has two sources. First, the patient's blood is hemodynamically unstable, which causes blood to shunt away from metabolically active tissues. These metabolically active tissues switch to anaerobic modes of respiration, which results in the production of lactic acid. Second, BAL hepatocytes contribute their own lactic acid to the circuit, probably because the BAL hepatocytes are not sufficiently oxygenated by the low oxygen tensions present in the BAL blood circuit.

Accumulation of lactic acid in a patient's blood can result in a highly undesirable lactic acidosis. Data from clinical trials has shown that rising concentrations of lactic acid in the BAL circuit can cause a substantial lowering of BAL circuit pH. This would be typically addressed by administering bicarbonate to the BAL circuit. However, the administration of free bicarbonate in the setting of lactic acidosis has been shown to sometimes produce decreases in intracellular pH with highly undesirable consequences on both brain and liver tissues. See, e.g., Forsythe, et al., Chest, 117:260-7 (2000).

A third issue associated with the use of a BAL device is cytokine activation. Cytokine activation has been observed upon initiating a number of extracorporeal treatments, including BAL treatments. Furthermore, acute and chronic liver failures manifest themselves as inflammatory reactions, which result in cytokine activation. Higher than normal concentrations of cytokines can be harmful to a variety of tissues. Cytokines that can be harmful include: Tumor Necrosis Factor-alpha (TNF-α), IL-1beta, IL-6, and others. Ways to control or eliminate above-normal levels of cytokines from patients undergoing treatment with a BAL device are highly desirable.

A fourth issue associated with existing BAL designs, is the problem of residence or contact time with the cultured hepatocytes of a BAL device. In some existing BAL designs, blood volume comes in contact with the hepatocyte compartment, sometimes referred to as the "bioreactor," only once. In some BAL designs where a patient's blood is separated into ultrafiltrate and concentrated blood fractions, only some 20-30% of blood volume withdrawn from the patient comes in contact with the hepatocytes in the bioreactor. According to the new methods and devices, blood volume has increased contact time with the hepatocytes in a BAL, which increases the opportunity for the hepatocytes in the bioreactor to perform their beneficial functions on a patient's blood.

Hemodialysis Recirculation Loops Can Address Some Problems Associated with BALs

The new hemodialysis (HD) recirculation loop described herein and the use of higher than atmospheric levels of oxygenation in a BAL circuit provide two means for addressing at least some of the issues associated with BAL devices described above. Supporting results are provided in the Examples below.

Hemodialysis devices have been shown to effectively remove both ammonia and free amino acids that contribute to a patient's free ammonia load. For example, continuous venovenous hemofiltration (CVVH) and continuous venovenous hemodiafiltration (CVVHD) have been shown to reduce levels of amino acids in the blood of children suffering acute renal failure. Maxvold et al., Critical Care Medicine 28:1161-5 (2000). Ahemofiltration device, used both with and without dialysis, was shown to reduce ammonia loads in patients being treated with a non-cell-based extracorporeal liver support device. Awad et al., Surgery, 130:354-362 (2001).

Hemodialysis devices have also been associated with the clearance of lactic acid from the bloodstream in patients suffering lactic acidosis. Barton et al., Nephrology dialysis transplant 6:368-70 (1991). Furthermore, hemodialysis devices have been shown to reduce the concentration of cytokines such as TNF-α, IL-6, and IL-10. Kellum et al., Crit. Care Med., 26:1995-2000 (1998).

The hemodialysis recirculation loop described herein exposes a portion of a patient's blood to multiple rounds of hemodialysis and/or hemofiltration. Multiple passes through the hemodialysis device increase the beneficial effects of hemodialysis and/or hemofiltration on the blood of a patient being treated with a bioartificial liver device. That is, the loop effectively increases the opportunities for the hemodialysis device to control excess ammonia, excess lactate, or excess inflammatory factors (e.g., cytokines) from a patient treated with a bioartificial liver device that includes a hemodialysis recirculation loop.

The hemodialysis recirculation loop also allows a portion of the patient's blood or ultrafiltrate (UF) fraction to make multiple passes through the hepatocyte chamber, or bioreactor, of the BAL. Multiple passes through the hepatocyte chamber results in increased effective contact time between hepatocytes and a portion of the patient's blood or UF relative to the contact time achieved by a BAL device, operating at the same blood processing rate, that allows only one pass of a patient's blood or UF through the bioreactor. Therefore, there are more opportunities for the hepatocytes to exert their beneficial effects on the portion of a patient's blood or UF that undergoes multiple passes through the bioreactor. For example, multiple exposures to hepatocytes imply more opportunities for liver cells to clear toxins, metabolize amino acids, and perform other functions on any given volume of a patient's blood or UF.

Use of Increased Oxygen Levels

Increasing the partial pressure of oxygen (e.g., from a normal oxygen concentration of about 21% to at least an oxygen concentration of about 26, 28, 30, 35, 40, 45, 50, 60, or 70%) available to hepatocytes in a bioreactor processing a patient's blood or UF fractions can reduce the loads of ammonia and lactic acid in the BAL circuit. Increasing the oxygen available to the hepatocytes in a BAL device reduces the need for those cells to engage in anaerobic respiration, increases the number of hepatocytes engaging in aerobic respiration, and thereby results in various advantages.

First, while not wanting to be bound by theory, we believe that inefficient hepatocyte function due to oxygen starvation causes BAL hepatocytes to produce more ammonia than they consume. Higher oxygen concentrations can thus reduce or eliminate the net contribution of ammonia by BAL hepatocytes to the BAL circuit. Second, limited oxygen availability causes the BAL hepatocytes to engage in anaerobic respiration that produces lactic acid and contributes to a patient's lactic acid blood load. Therefore, higher oxygen levels can reduce the number of hepatocytes that engage in anaerobic respiration, and thereby reduce the number of hepatocytes contributing lactic acid to the BAL circuit. Third, by shifting more hepatocytes to aerobic respiration, higher oxygen levels increase the energy available (in the form of more ATP and NADH) for hepatocytes to perform the anabolic and catabolic reactions involved in fixing ammonia and consuming lactic acid. Therefore, increasing the partial pressure of oxygen available to BAL hepatocytes causes the hepatocytes to actively consume ammonia and lactate in a BAL-supported patient's blood stream.

Methods of delivering higher partial pressures of oxygen to hepatocytes can include: adding gas with higher than atmospheric concentrations of oxygen to the ultrafiltrate before the ultrafiltrate is passed to the bioreactor, adding higher than atmospheric concentrations of oxygen to the ultrafiltrate while the ultrafiltrate is in the bioreactor, or adding higher than atmospheric concentrations of oxygen to the bioreactor as it processes ultrafiltrate. Any combination of two or more of the described methods of delivering oxygen to the hepatocytes can also be used.

Techniques for oxygen delivery are well known. In one of many examples, an oxygen tank can be used to bubble a gas with higher than atmospheric concentrations of oxygen into the ultrafiltrate, into the hepatocyte chamber of a bioreactor, or into both the UF and the hepatocyte chamber. Methods for monitoring oxygen delivery are also well known, and include, but are not limited to, using oxygen sensors to measure oxygen concentration. Gases with a higher than atmospheric concentration of oxygen that are suitable for use with a BAL device are described in Example 2; and they can also include a gas with any oxygen concentration greater than or equal to about 26, and less than about 79%. For example, oxygen concentrations can be anywhere between about 26% and 70%, or anywhere between 30% and 60%. Exemplary higher than atmospheric concentrations of oxygen include oxygen concentrations of about 28, 30, 35, 40, 50, 52.6%, or more.

As used herein, "higher than atmospheric partial pressure of oxygen" and "higher than atmospheric concentration of oxygen" are used interchangeably. A concentration of oxygen denotes the percent fraction of atmospheric pressure due to oxygen. For example, if atmospheric pressure is 760 mm Hg, and it is disclosed that a gas has "a concentration of oxygen that is 30%," then the partial pressure due to oxygen is 30% of 760 mm Hg, i.e., 228 mm Hg.

Figure 2:
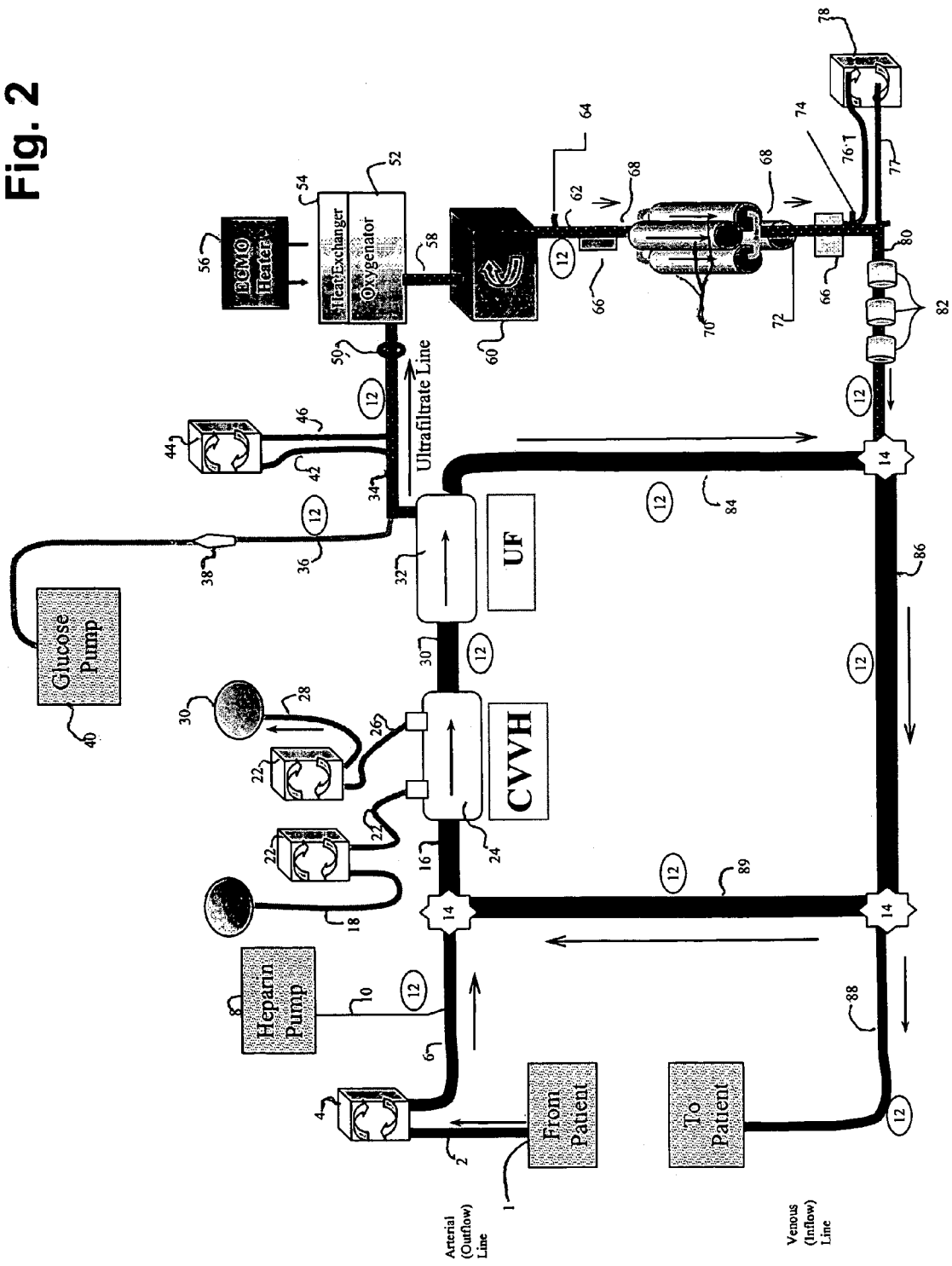
FIG. 2 is a schematic diagram of one configuration for a bioartificial liver support system with a hemodialysis recirculation loop that exposes a fraction of a patient's blood to multiple passes through both a hemodialysis system and a liver assist device.

General Configuration and Detailed View of a BAL with a Hemodialysis Recirculation Loop FIG. 2 shows a BAL device with a new HD recirculation loop. Blood withdrawn from a patient is processed by a hemodialysis device (16, 18, 22, 24, 26, 28, and 30) before it reaches the ultrafiltrate generator 32. Dialyzed fluid is divided into a UF fraction and a concentrated blood fraction. UF passes through the bioreactor compartment 70 of the BAL, and is subsequently remixed with the concentrated blood fraction to form processed whole blood. Unlike currently used BALs, only one portion of the processed whole blood is returned to the patient through a line 88. The other portion of the processed whole blood is circulated through a line 89 to a T-connector or three-way stopcock 14 that mixes the processed whole blood with unprocessed venous blood from the patient in lines 6. This mixture of processed blood and newly drawn blood is carried by line 16 to the dialysis device (16, 18, 22, 24, 26, 28, and 30). Thus, the HD recirculation loop creates a semi-closed circuit or conduit that ensures that some portion of a patient's drawn blood is exposed to multiple rounds of hemodialysis and multiple exposures to living hepatocytes before the drawn blood is returned to the patient.

In particular, FIG. 2 shows a schematic view of the blood flow circuit of a BAL device outfitted with a new HD recirculation loop as described herein. An arterial line 2 withdraws blood from a patient through a double lumen venous catheter 1 (or any other suitable means of withdrawing blood from a patient's vein). The flow of blood through the arterial line is aided by a blood pump 4. After being withdrawn from a patient, blood is thinned by adding thinning compounds, such as heparin and/or citrate. For example, heparin can be added by a heparin pump 8 through line 10. Heparinized blood is carried by line 6 to a connector 14 joining line 6, line 89, and line 16. The connector may be a T-connector or three-way stopcock, e.g., a stopcock capable of selectively allowing for fluid from line 89 to mix with the fluid from line 6 into a mixture that flows down line 16, or for fluid from line 6 to flow unmixed into line 16.

Blood in line 16 passes through a hemodialysis device, e.g., a continuous venovenous hemofiltration (CVVH) device 24, attached to a dialysis supply tube 22 and a dialysate waste tube 26. Dialysis fluid is supplied via line 18, whose flow is controlled by a pump 20 into the dialysis supply tube 22, which feeds the CVVH 24. Dialysate waste is carried from the CVVH by line 26, whose flow is controlled by a pump 20 into line 28 and into a dialysate waste 30. Blood that has been dialyzed in the CVVH is passed by line 30 to an Ultrafiltrate (UF) generator 32. The UF generator separates blood into a concentrated blood fraction, which is discharged into line 84, and an ultrafiltrate fraction, which is discharged into UF line 34. Glucose can be added to the UF from a glucose pump 40 via a glucose infusion line 36. The flow of glucose into line 34 can be controlled by a ratchet clamp 38. The flow of ultrafiltrate in line 34 is controlled by a UF pump 44 that draws UF from line 34 via line 42, and returns UF to the ultrafiltrate line 34 via line 46. Leaks along the UF line are monitored by blood leak detector 50. UF can then enter an oxygenator/warmer compartment 52. A heat exchanger 54 in the oxygenator/ heater compartment is warmed by an external Extracorporeal Membrane Oxygenation (ECMO) heater 56.

Warmed and oxygenated UF is passed through a line 58 to a centrifugal pump 60. Centrifuged UF is discharged from the centrifugal pump into the hepatocyte compartment's bioreactor's inlet line 62, which includes a sampling port 64 that can be used to monitor the characteristics of UF before it is exposed to hepatocytes in one or more bioreactor compartments 70.

In-line gas analyzers 66 are placed along the bioreactor's inlet line 62 and the bioreactor's outlet line 72. The bioreactor's inlet line 62 and outlet line 72 are connected to the bioreactor 70, e.g., by quick disconnects 68. The bioreactor outlet line 72 can include a sampling port 74. The flow of UF that has been exposed to the hepatocytes in the bioreactor (processed UF) can be adjusted using a pre-filter pump 78, which draws UF from line 72 via line 76, and returns UF to the filter line 80 via line 77.

An in-line series of cell filters 82 can be located along the filter line 80. Processed UF is then mixed with the concentrated blood fraction that was generated by the UF generator 32. The concentrated blood fraction from the UF generator is carried by the concentrated blood fraction line 84 to a T connector or three-way stopcock 14 joining lines 84, 80, and 86. The concentrated blood from line 84 and the processed UF from line 80 are mixed to form processed whole blood which is carried by line 86 to a third T connector or three-way stopcock 14 joining lines 86, 87, and 89, where the processed whole blood is divided into two portions. One portion is carried by line 89 to the first T-connector 14 or three-way stopcock that joins lines 89, 6, and 16, while the second portion is carried by line 88 back to the patient.

As is apparent from FIG. 2, the hemodialysis recirculation loop described herein represents a semi-closed circuit of dialyzed blood and dialyzed blood fractions. The semi-closed circuit can be readily seen by following the flow of blood (represented by arrows adjacent to lines) through lines 16, through line 84 and concurrently through the hepatocyte chamber 70 and line 80, then though line 86, and then back through line 89. When blood flows from line 89 back into line 16, the blood has completed one cycle through the hemodialysis recirculation loop. The loop allows a patient's blood to not only be dialyzed more than once, but also allows for multiple passes of a patient's blood through the hepatocyte chamber or bioreactor of a BAL device.

Figure 3:
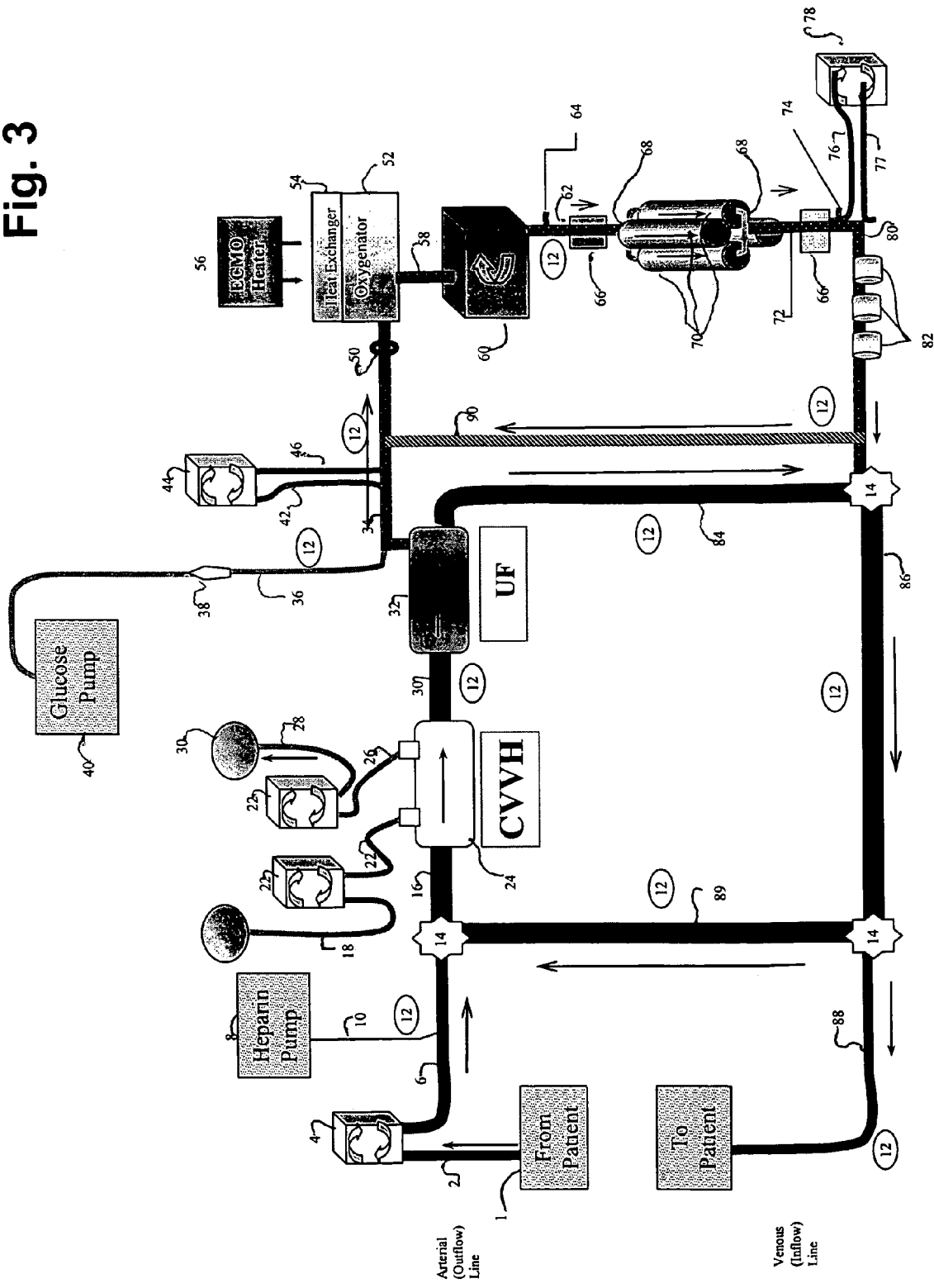
FIG. 3 is a schematic diagram of one configuration for a bioartificial liver support system with a hemodialysis recirculation loop and a post-bioreactor recirculation line. The post bioreactor recirculation line creates a second closed loop that allows for multiple passes of ultrafiltrate through the heater-oxygenator systems and the bioreactor.

FIG. 3 shows a schematic view of the same BAL device shown in FIG. 2, to which has been added a post-bioreactor recirculation line 90. The post-bioreactor recirculation line creates a semi-closed circuit of UF flow that allows for multiple passes of heated and oxygenated UF through the bioreactor. Although in FIG. 3 the post-bioreactor recirculation line 90 is shown drawing UF from line 80 after the UF has passed through the in-line cell filters 82, the post bioreactor recirculation line may also draw UF from any location upstream of the in-line cell filters and downstream of the bioreactor.

Figure 4:
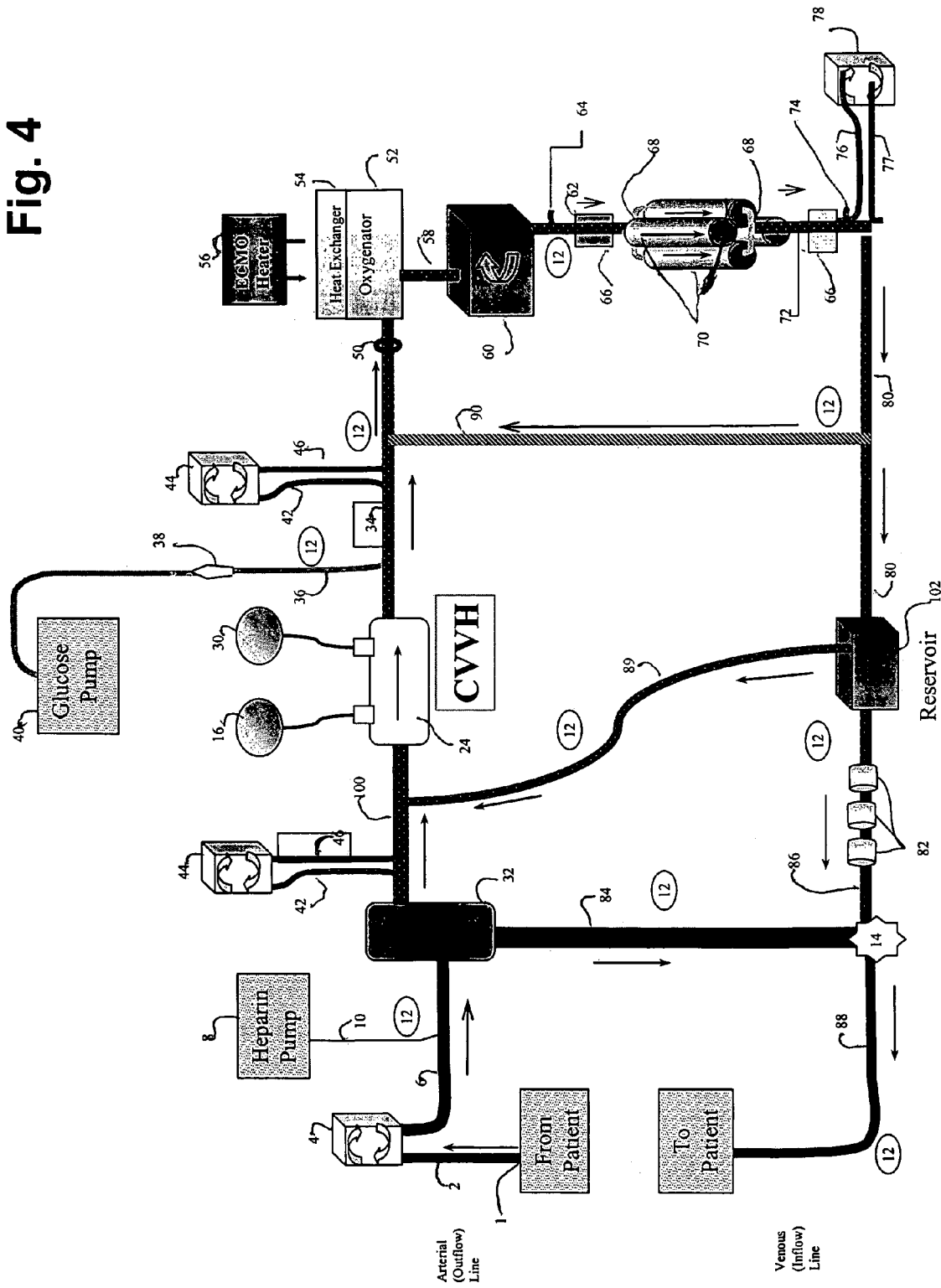
FIG. 4 is a schematic diagram of another configuration for a bioartificial liver support system with a hemodialysis recirculation loop and a post-bioreactor recirculation line.
Figure 5:
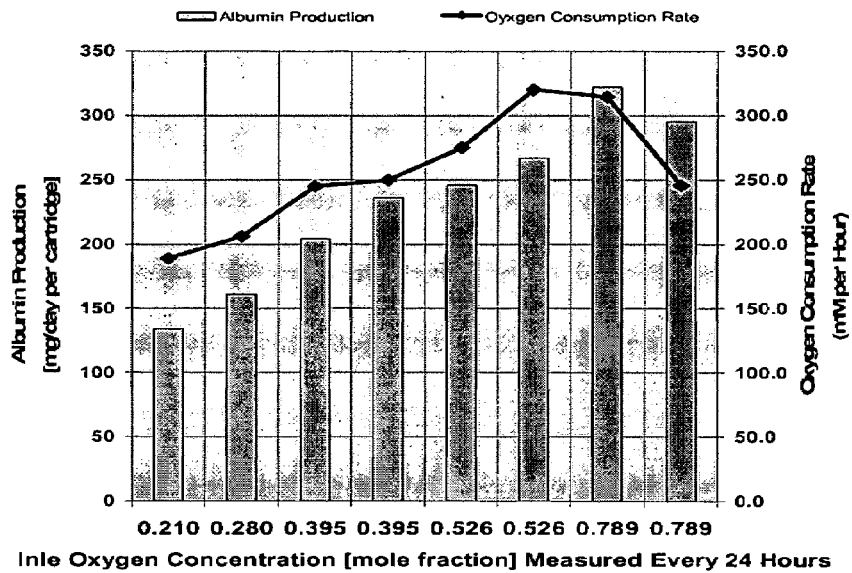
FIG. 5 is a chart tracking albumin production data against the oxygen consumption rate data given in Table 2.
Figure 6:
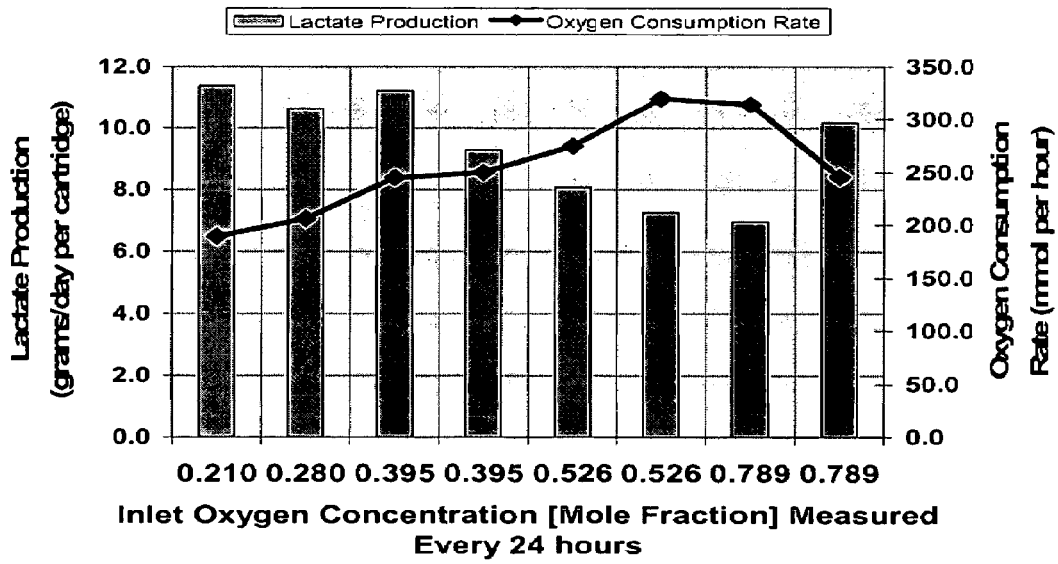
FIG. 6 is a chart tracking lactate production data against the oxygen consumption rate data given in Table 2
Figure 7:
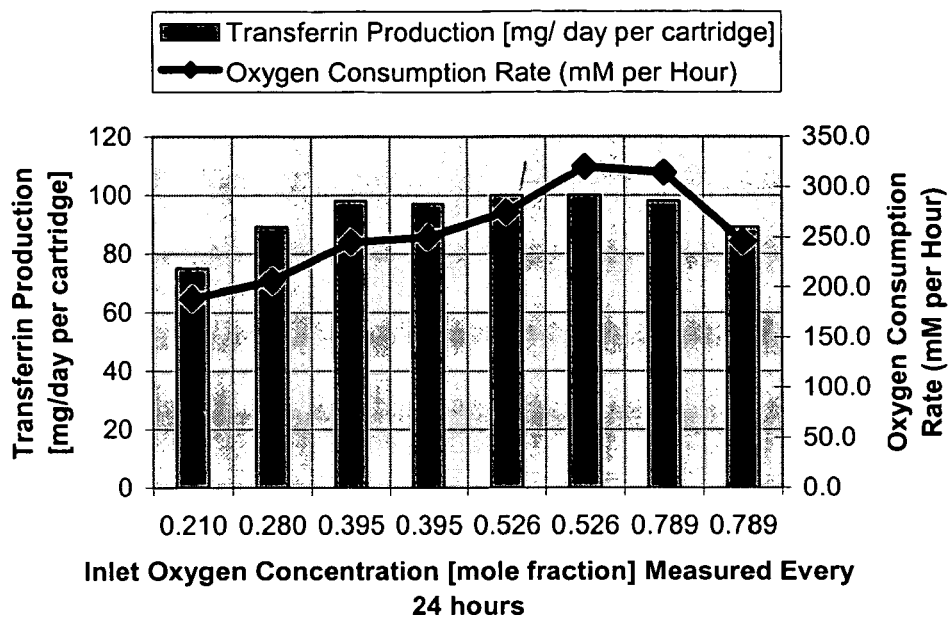
FIG. 7 is a chart tracking transferring production data against the oxygen consumption rate data given in Table 2.
Figure 8:
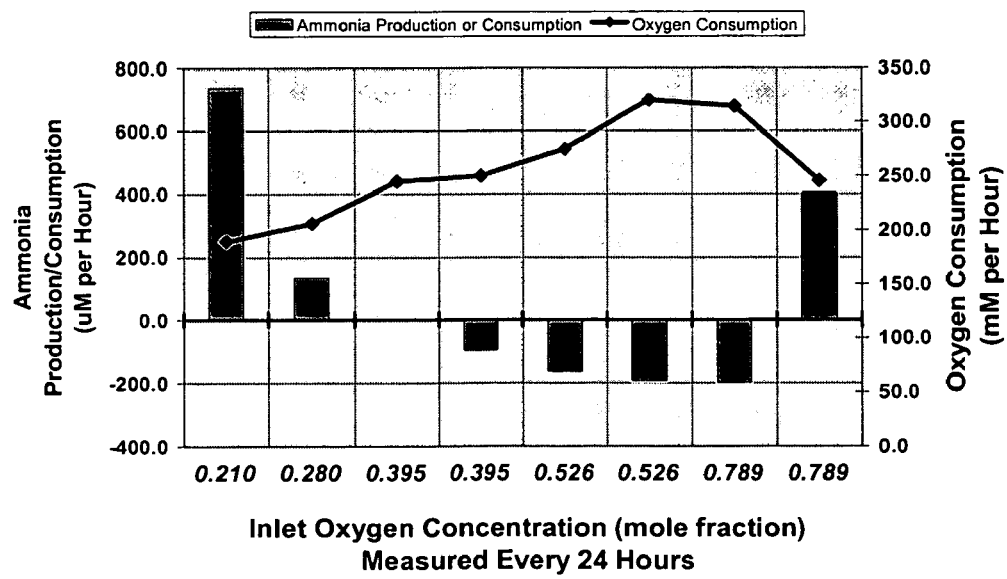
FIG. 8 is a chart tracking ammonia production/consumption data (waste ammonia subtracted from feed ammonia) against the oxygen consumption rate data given in Table 2.
Figure 9:
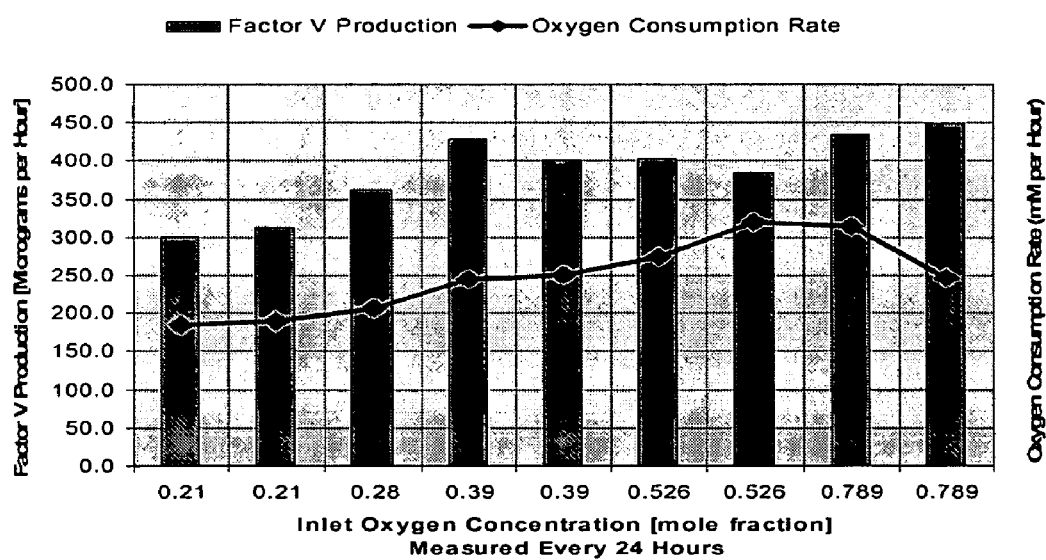
FIG. 9 is a chart tracking factor V production data from Table 3 against the oxygen rate consumption data from the same experiments.

FIG. 4 shows a schematic view of an alternate configuration for a BAL device with an HD recirculation loop and a post-bioreactor recirculation line. In this configuration, blood from a patient in line 6 is carried to a UF generator 32, which generates a UF fraction carried by line 100, and a concentrated blood fraction carried by line 84. UF in line 100 is dialyzed, e.g., by a CVVH device, which is subsequently carried to the bioreactor 70. Bioreactor-processed UF is carried by line 80 to a reservoir 102. The alternate configuration may optionally have a post-bioreactor recirculation loop 90, which can draw a portion of the bioreactor processed UF, before it reaches the reservoir 102, and return the UF to line 34, thus allowing a portion of the bioreactor processed UF to undergo multiple passes through the bioreactor. Bioreactor processed UF in the reservoir is divided into portions, one portion of which can return to line 100 via the HD recirculation line 89, for multiple dialysis/CVVH treatments and multiple passes through the bioreactor. The other portion of bioreactor processed UF in the reservoir is carried by line 86, through a series of in line cell filters 82, and the filtered UF can be recombined with the concentrated blood fraction in line 84. The mixture of UF from line 86 and concentrated blood from line 84 is returned to the patient.

Flow Rates through a BAL Device with an HD Recirculation Loop

The present disclosure describes a hemodialysis (HD) recirculation loop that increases the beneficial effects of both a hemodialysis device and a bioreactor in a BAL system. The HD recirculation loop ensures that at least some portion of a patient's blood that is withdrawn is exposed to multiple treatments by the hemodialysis device and the bioreactor compartment of a BAL, before the blood is returned to the patient. Nevertheless, any sustained extracorporeal blood treatment must ensure that, when the treatment system reaches steady state, the amount of blood withdrawn from a patient is equivalent to the amount of blood being returned to the patient. The new devices and methods achieve both of these effects by running blood through the closed hemodialysis recirculation loop at a higher flow rate relative to the patient inlet and outlet flow rates.

For example, the flow rate within the hemodialysis recirculation loop (HD flow rate) can be any flow rate that is from approximately 0.1 to approximately 10 times the blood inlet and blood outlet flow rates (patient flow rate), e.g. the ratio of HD flow rate to patient flow rate can be approximately any of the following ratios: 0.1 to 1, 0.2 to 1, 0.5 to 1, 0.7 to 1, 0.9 to 1, 1.1 to 1, 1.5 to 1, 2 to 1, 3 to 1, 4 to 1, 5 to 1, 6 to 1, 7 to 1, 8 to 1, 9 to 1, or 10 to 1. In other words, the HD flow rate is at least 10% faster than the flow rate of blood from the patient into the BAL circuit and the flow rate of blood returning to the patient from the BAL circuit. By running fluids through the hemodialysis recirculation loop at this higher relative rate, the use of the HD recirculation loop increases the probability that any given volume of blood, or blood fraction, will contact the hepatocytes in the bioreactor and will be filtered by the hemodialysis device multiple times. Referring to FIG. 2, the flow rate through the closed loop that includes lines 16, 84, 86, and 89 can be 2 to 10 times faster than the flow rate through line 2 and line 88.

The flow rate through an organ assist device with an HD recirculation loop can be controlled using a commercially available perfusion system designed to control blood flow through an extracorporeal blood circuit. One among several examples of such a system is a heart-lung machine, e.g., the Terumo® Advanced Perfusion System 1 (Terumo Cardiovascular Systems Corp., Ann Arbor, Mich.) that allows blood flows to be monitored and controlled from a central console linked to digitally controlled pumps, which, after calibration, can control multiple flow rates within a circuit, including the dialysis/CVVH pump controls as well as flow rates through the rest of an organ assist device equipped with an HD recirculation loop.

Other Modifications of a BAL Device to Remove Cytokines

In some embodiments, a BAL device can be further outfitted with one or more filtration devices to remove harmful cytokines from a BAL circuit. As described above, chronic, acute, and acute-on-chronic liver failures are associated with inflammatory reactions that can activate TNF-α, IL-1β, IL-6, and other cytokines. These cytokines can lead to the damage of a number of different tissues in a patient.

In addition to a CVVH device, other filtration devices can be used in a BAL device to reduce cytokines in a patient's blood serum. Generally these filtration devices remove, by adsorption or binding to, one or more harmful cytokines from a patient's blood or blood fraction. A cytokine filtration device can be placed along any of the lines in a BAL device in such a way that blood or a blood fraction passes through the device.

A cytokine filtration device can be made, for example, by immobilizing on a substrate a compound that adsorbs or binds to one or more harmful cytokines. The substrate can be placed in a column or chamber to form a filtration device. Compounds that bind to a harmful cytokine include, but are not limited to, anti-cytokine (e.g., anti-TNF-α; anti-IL-1β, and/or anti-IL-6) antibodies, cytokine receptors (e.g., TNF-α, IL-1β, and/or IL-6 receptors), ligand-binding portions of cytokine receptors, and, in some cases, "cytokine traps" that contain fused ligand-binding portions (e.g., the extracellular domains) of two or more cytokine receptors.

A cytokine filtration device can also be a column or chamber that contains a membrane or fiber that adsorbs one or more harmful cytokines. For example, polysulfone, polyacrylonitrile, polyamide and cellulose triacetate are compounds that have been reported to adsorb cytokines and can be formed into fibers (e.g., hollow fibers) or membranes.

USES OF THE INVENTION

1. Liver Failure

The methods and devices described herein improve the function of organ assist devices used to treat conditions arising from organ dysfunction and sometimes associated with hemodynamic instability. In one example, the methods and devices disclosed herein can be used with liver support devices used to treat liver failure. These methods and devices are useful in the treatment of patients suffering from any of the following conditions: chronic liver disease, cirrhosis, acute exarcebations of chronic liver failure (i.e., acute-on-chronic liver failure), and acute or fulminant hepatic failure. See for example U.S. Pat. Nos. 5,290,684; 6,458,589 Fulminant hepatic failure may be due to any of a number of different causes, including viral infections (e.g., hepatitis), drugs, or toxins. Patients with any of the conditions listed can progressively worsen until they require orthotopic liver transplantation.

The methods and devices of the present invention can be used with a liver support device to provide a "bridge" that can support a patient during the period of time that follows acute liver failure and lasts until a donor liver becomes available for orthotopic transplantation. Several bioartificial liver devices have been or are currently undergoing clinical studies to support patients awaiting liver transplants. Examples of devices that have been tested as a "bridge" device for transplant candidates include: Vital Therapies Inc.'s (San Diego, Calif.) Extracorporeal Liver Assist Device™ (ELAD™), Circe Biomedical's (Lexington, Mass.) HepatAssis™, Excorp Medical's (Oakdale, Minn.) Bioartificial Liver Support System™ (BLSS), and the Bioreactor Extracorporeal Liver Support System (BELS) described in Sauer, et al., Annals NY Acad Sci. 944:308-19 (2001).

Other devices that have been tested on patients with acute liver failure include the Bio-Logic DT (HemoCleanse Inc., West Lafayette, Ind.) and the Molecular Adsorbent Recirculating System (MARS) described in Schachschal, et al., Liver 22(Suppl 2):63-68 (2002). The devices and methods disclosed herein can be easily modified for use with any of the devices disclosed above, and similar organ support devices, to support a patient in need of a liver transplant, until the time a donor liver becomes available.

The new methods and devices can also be used in conjunction with an artificial or bioartificial liver support device to support patients that "spontaneously" recover from liver failure without the need for a transplanted liver. For example, one retrospective study found that in a population of patients diagnosed with acute liver failure, 14% survived with only medical management, without the need for transplantation. Shakil et al., Dig. Dis. Sci., 45(2):334-9 (2000). By improving the function of a BAL device the present invention can provide a bridge to recovery by replacing essential liver functions in patients suffering from liver failure until the patient's own liver recovers.

The new methods and devices can also be used to help support liver function in patients who have undergone liver transplantation. The new methods and devices can replace or supplement essential liver functions in allograft recipients until that time when the allograft becomes sufficiently functional.

The new methods and devices can also provide a "bridge" to help support liver function in patients who undergo split-liver transplants. In split-liver transplants, a single donor organ is divided into two, or more, portions and each portion is transplanted into a different patient. The procedure takes advantage of the liver's ability to regenerate itself, even after losing a majority of its tissue. Split-liver transplants hold the potential to effectively double, triple (or theoretically multiply by four times or more) the available donor organ pool. Because split-liver allograft recipients are less likely than whole liver transplant recipients to quickly regain normal liver function after transplantation, the present invention can be used in conjunction with an organ support device to provide a more effective "bridge" to recovery by replacing essential liver functions in allograft recipients during the period needed for the split-liver to sufficiently regenerate tissue mass and/or become sufficiently functional.

2. Pancreatitis, Sepsis, Autoimmune Disorders

The devices disclosed herein can also be used to treat patients suffering from conditions associated with compromised liver function, including, but not limited to, pancreatitis, sepsis, and autoimmune disorders. These conditions can lead to severe and sometimes lethal hemodynamic instabilities.

Acute pancreatitis progresses from local acinar injury, to systemic inflammatory response, and finally to generalized sepsis. This progression is the result of a pro-inflammatory response that triggers a massive follow-on anti-inflammatory response. Both inflammatory responses are mediated by a succession of different cytokines. The inflammatory cascades that result in the release of large amounts of cytokines are sometimes referred to as "cytokine storms," and they can lead to multiple organ dysfunction.

The methods and systems of the present invention can improve the treatment of patients with acute pancreatitis in two ways. First, as discussed above, the hemodialysis recirculation loop disclosed herein provides a mechanism for clearing, at least some, of the cytokines from a patient's blood stream. Thus, an organ assist device outfitted with an HD recirculation loop provides a method of dampening the effects of a "cytokine storm" by removing cytokines from the blood of a patient suffering from acute pancreatitis, thereby preventing or lessening the severity of a pancreatitis-induced inflammatory response. Second, a BAL device outfitted with any of the improvements disclosed herein, e.g. with an HD recirculation loop and/or with higher than atmospheric oxygen concentrations, provides a method of supplementing or supporting liver function in acute pancreatitis patients. The liver is also associated with cytokine clearance, thereby supplementing a pancreatitis patients' liver functions may reduce the impacts of cytokine storms. Additionally, the liver is frequently one of the organs affected in pancreatitis-induced multiple organ dysfunction. Therefore, the BAL devices and methods for using them disclosed herein, can support pancreatitis patients suffering from impaired liver function.

Sepsis has numerous causes, e.g., viral, bacterial, fungal, post-operative infection, injury infection, and many more. Like pancreatitis, sepsis can also be characterized by very strong cytokine-mediated inflammatory response and can lead to multiple organ failure. Therefore, in the same ways listed for pancreatitis, the methods and devices disclosed herein can be used to clear cytokines from the blood of septic patients using the HD recirculation loops and/or hepatocyte function of a liver assist device. Additionally, the newly modified BAL devices of the present invention can be used to support patients with sepsis-induced liver failure, e.g., as part of sepsis-induced multiple organ failure treatment.

Several autoimmune diseases are also known to affect liver function, e.g., autoimmune hepatitis and HIV-HCV coinfection. The methods and devices disclosed herein can also provide support or replace liver function in patients suffering from autoimmune disease-mediated liver failure.

EXAMPLES

The invention is further described in the following examples, which do not limit the scope of the invention described in the claims.

Example 1

Clearance of Ammonia and Lactate by a Bench-top ELAD™ Device Outfitted with a Hemodialysis Recirculation Loop The following example demonstrates the capacity of a continuous veno-venous hemodialysis device (CVVH) to clear ammonia and lactate from the blood flow circuit of a bioartificial liver (BAL) device outfitted with an HD recirculation loop. The experiment was performed on a bench-top version of the ELAD™ liver support device (Vital Therapies, Inc., San Diego, Calif.) outfitted with an HD recirculation loop similar to the one described in FIG. 3, with the following modifications. The arterial line 2 was connected to a Feed Carboy to model the patient's contribution of ammonia and lactate to the system. Instead of ELAD™ cartridges, i.e., the bioreactor 70, the bioreactor inlet 62 and outlet 72 lines were connected to three bags, referred to below as ELAD™ bags, which modeled the bioreactor's contribution of lactate and ammonia to the system. Levels of ammonia and lactate were monitored at three different points in the system: at the patient return line 88, along the HD recirculation line 87, and at the CVVH waste 30.

At the beginning of the experiment, the Feed Carboy contained a saline solution with supra-physiological concentrations of both ammonia and lactate that was replenished during the experiment. The following concentrations of ammonia and lactate were fed into the ELAD™ device circuit by the Feed Carboy at different times throughout the experiment:

at t=0: 610 µM Ammonia and 16.6 mM Lactate
at t=60: 540 µM Ammonia and 8.1 mM lactae
at t=120: 580 µM Ammonia and 7.1 mM Lactate
at t=130: 582 µM Ammonia and 8.9 mM Lactate In a functioning ELAD™ device, individual hepatocyte cartridges produce different amounts of ammonia and lactate, likely due to variations in hepatocytes numbers and/or metabolic activity. Therefore, at t=0, ELAD™ bags in this experiment contained saline solutions with a range of ammonia and lactate concentrations. The concentrations were:

ELAD™ bag No 1: 468 µM ammonia and 25.3 mM Lactate
ELAD™ bag No 2: 379 µM ammonia and 40.4 mM Lactate
ELAD™ bag No 3: 366 µM ammonia and 10.2 mM Lactate Results The data provided in Table 1 show that an HD recirculation loop, with a CVVH device, continuously reduced the concentration of both ammonia and lactate in the patient return line and the HD recirculation line over a period of 2 hours. The data also showed that the CVVH device effectively removed both ammonia and lactate from the ELAD™ flow circuit as demonstrated by the continuous flow of ammonia and lactate into the CVVH waste.

The overall clearance rates of ammonia and lactate in this experimental system, using two different rates of CVVH, were calculated from the data in Table 1. Clearance rates are expressed in milliliters of serum/media cleared of the toxin each minute (i.e., ml/min)

Clearance rate of Ammonia with an HD recirculation Loop
at 2400 cc/hour: 57.2 ml/min
at 3200 cc/hour: 62.8 ml/min Clearance rate of Lactate with an HD recirculation Loop
at 2400 cc/hour: 44.3 ml/min
at 3200 cc/hour: 48.9 ml/min The clearance rates shown above compare favorably with the clearance rate observed in an ELAD™ system that was outfitted only with a single-pass CVVH (i.e., the system lacked the HD recirculation line 87 depicted in FIG. 3.) In this single-pass CVVH system the calculated clearance rates at a CVVH intensity 3200 cc/hour were:

Ammonia: 38.6 ml/min Lactate: 42.6 ml/min

The experiment demonstrates that the HD recirculation loop has a positive impact on clearance rates, and in particular on the ammonia clearance rate, which significantly exceeds the effect of placing only a single-pass CVVH device along the ELAD™ circuit.

TABLE 1

| Time Minutes | Patient Return [Ammonia] µM | CVVH Waste [Ammonia] µM | Recirculation [Ammonia] µM | Patient Return [Lactate] mM | CVVH Waste [Lactate] mM | Recirculation [Lactate] mM |
|---|---|---|---|---|---|---|
| 0 | 470 | — | 470 | 16.8 | — | 17.3 |
| 15 | 400 | 390 | 387 | 12.8 | 13.1 | 12.4 |
| 30 | 381 | 370 | 380 | 11.6 | 10.5 | 10.1 |
| 45 | 372 | 370 | 370 | 9.3 | 8.4 | 8.6 |

TABLE 1-continued

| Time Minutes | Patient Return [Ammonia] μM | CVVH Waste [Ammonia] μM | Recirculation [Ammonia] μM | Patient Return [Lactate] mM | CVVH Waste [Lactate] mM | Recirculation [Lactate] mM |
|---|---|---|---|---|---|---|
| 60 | 361 | 360 | 368 | 8.0 | 7.3 | 7.1 |
| 75 | 345 | 340 | 359 | 7.4 | 6.6 | 6.6 |
| 90 | 335 | 331 | 335 | 7.4 | 6.5 | 6.6 |
| 105 | 331 | 336 | 335 | 8.4 | 6.6 | 7.0 |
| 120 | 330 | 333 | 333 | 7.2 | 6.7 | 6.4 |
| 135 | 315 | 318 | 332 | 7.8 | 6.9 | 7.0 |

Example 2

Higher than Atmospheric Partial Pressures of Oxygen

The following example demonstrates the beneficial impact of introducing higher than atmospheric oxygen concentrations to a BAL bioreactor.

An oxygen tank line was connected to an inlet line leading to 4 ELAD™ cartridges. Hepatocytes in the cartridges were grown for 26 days at slightly higher than atmospheric partial pressures of oxygen (oxygen concentration was 21-26%) to allow the cells to reach a cell growth plateau. On days 26, 27, 29, and 31 the percent of oxygen introduced to the line was stepped up to the levels indicated (DO1) in Table 2. Also, on day 26, a saline solution containing ammonia was fed to the cartridges' inlet line to model the ammonia load in UF passing through the cartridges in a clinical BAL device. After passing through the bioreactor cartridges, the oxygen levels in the saline solution leaving the cartridges were measured, (DO2) and saline solution was collected in a waste container. Ammonia, lactate, transferring, and albumin were measured in the collected "waste" saline.

Results

1. Ammonia

Increasing the partial pressure of oxygen in the hepatocyte chambers markedly improved the ability of the bioreactor's hepatocytes to metabolize ammonia. Results are shown in Table 2. Before stepping up oxygen levels on day 26, the bioreactor generated more ammonia than it metabolized. Upon challenging the cartridges with an ammonia concentration in feed saline of ~0.5 mM, for a total ammonia load rate of 9.6 μmole/hour, the ammonia concentration in waste was measured at 1.1 mM at 24 hours. This result indicates not merely inefficient metabolism of ammonia by the bioreactor hepatocytes, but also that the bioreactor itself contributes a net increase to ammonia levels.

When the concentration of oxygen in the gas mixture added to feed saline was increased to 28% for 24 hours, and the feed concentration of ammonia was held steady at ~0.5 mM, the concentration of ammonia measured in waste saline declined significantly to ~0.6 mM. Thus, the rate of ammonia metabolism increased, relative to the rate of ammonia produced by the hepatocytes in the system, when oxygen concentration increased.

The trend continued when oxygen levels were increased further to ~40%. After 24 hours at 40% oxygen the system showed no net production of ammonia, as feed and waste ammonia concentrations were both 0.486 mM. After 48 hours of 40% oxygen (day 29), the system appeared to be consuming ammonia; as waste concentration, 0.448 mM, was slightly lower than the feed ammonia concentration 0.486 mM.

At 52.6% oxygen, the system demonstrated significant capacity to metabolize ammonia. After 24 hours at 52.6%, and while feed ammonia concentration was increased to 0.529 mM, the waste ammonia concentration declined to 0.392 mM. During the second 24 hour period of 52.6% oxygen, feed ammonia concentration was increased slightly to 0.554 mM, and waste ammonia was measured at 0.394 mM. This represents an increase in the net quantity of ammonia metabolized by the hepatocytes in the face of higher ammonia concentration.

Interestingly, no further significant increase in net ammonia metabolism was observed after stepping the oxygen concentration level to 78.9% for 24 hours. In fact, after 48 hours at 78.9% oxygen, the bioreactor was producing more ammonia than it was consuming, as waste ammonia readings increased to 0.897 mM, while feed ammonia concentration was 0.561 mM.

2. Oxygen Consumption

Percent oxygen in saline going into the cartridges (DO1) and out of the cartridges (DO2) was monitored. The difference between these two concentrations (DO1-DO2) reflects oxygen consumption, i.e., aerobic respiration, by the hepatocytes. The results in Table 2, indicate that oxygen was limiting at concentrations of 39.5% and below. When the oxygen concentration was elevated to 52.6%, the system demonstrated its highest levels of oxygen consumption (largest DO1-DO2), among oxygen levels tested.

Interestingly, the rate of oxygen consumed by the system declined as oxygen percentage was elevated to 78.9%, suggesting that too much oxygen can have a toxic and/or inhibitory effect on the aerobic metabolism of hepatocytes in a bioreactor.

3. Lactate

Levels of lactate in waste saline saw their sharpest drop after oxygen levels had been stepped up to 39.5% for 40 hours. They continued to drop as oxygen levels were increased to 52.6% for 48 hours, and then stepped up to 78.9% for 24 hours. Nevertheless, lactate produced in the bioreactor spiked after 48 hours of 78.9% oxygen. The lactate results are largely consistent with the oxygen data. As cells consumed more oxygen (DO1-DO2%), they tended to produce less lactate. This trend is consistent with the notion that oxygen is limiting at concentrations of 39.5% and less. As cells are given more oxygen and more cells shift from anaerobic metabolism to aerobic metabolism the level of lactate is expected to decrease. The fact that lactate levels went up after 48 hours at 78.9% oxygen parallels the decline in oxygen consumption observed, and independently suggests that prolonged exposure to oxygen levels above of 78.9% has a toxic and/or inhibitory effect on hepatocyte aerobic respiration.

4. Albumin & Transferring

Levels of albumin and transferring in the waste were measured as indirect indicators of hepatocyte health and/or metabolic activity. Increases and decreases in transferring production by the hepatocytes strictly tracked increases and decreases of hepatocyte oxygen consumption, thereby providing another indication that hepatocytes in the ELAD bioreactor operate optimally at higher than atmospheric partial pressures of oxygen. Increases and decreases in albumin production levels also generally tracked increases and decreased in oxygen consumption.

The data in Table 2, as discussed above, are consistent with the idea that the bioreactor in a BAL device can contribute to the ammonia and lactate loads of patients being treated with such a device. Furthermore, the data suggest that this detrimental circumstance may be due to the apparent oxygen starvation of at least some BAL hepatocytes, in BAL configurations that do not provide higher partial pressures of oxygen to the hepatocytes. Increasing the partial pressure of oxygen in fluid entering a bioreactor was shown to alleviate the apparent oxygen starvation with the following encouraging results: levels of ammonia and lactate produced by the system declined, and positive markers of hepatocyte health/metabolism increased.

score that the United Network for Organ Sharing (UNOS) uses to assess patient mortality risk and to prioritize candidate liver transplant recipients suffering from acute or acute on chronic liver failure. Thus, factor V is a sensitive indicator of hepatocyte health that can track changes in the health of hepatocytes that are in a state of flux.

Four ELAD cartridges were arranged as described in Example 2. To allow ELAD hepatocytes to reach a cell growth plateau, the oxygen feed to the ELAD's inlet line was maintained for 26 days at slightly higher than atmospheric partial pressures of oxygen (oxygen concentration was 21-26% $FiO_2$, i.e., percent concentration of oxygen in the feed gas). On day 26, the percent of oxygen introduced to the inlet line was adjusted, in 48 hour steps, to the levels indicated ($FiO_2$) in Table 3. Levels of factor V in the media going into the ELAD cartridges ($DO_1$) and emerging from the ELAD cartridges ($DO_2$) were measured using a commercial Factor V enzyme linked immunosorbent assay (ELISA) (FV EIA™ from Affinity Biologicals, Ancaster, ON, Canada). Total factor V levels were measured as a function of ($DO_2$-$DO_1$), which is shown as µg/total in Table 3. Assuming a media flow rate of 20 cc/min, factor V production as a function of time was also calculated, as shown in the µg/min and µg/hour columns of Table 3.

ELISA measurement of factor V was performed essentially as described by the manufacturer, except that incubation with primary antibodies was done in 75 minutes. A

TABLE 2

|  | Feed Ammonia mM/L | Waste Ammonia mM/L | DO1 % (inlet) | DO2 % (outlet) | (DO1-DO2) % | Lactate mM/L | Albumin mg/day/ cartridge | Transferrin mg/day/ cartridge |
| --- | --- | --- | --- | --- | --- | --- | --- | --- |
| Day 26 | 0.486 | 1.100 | 26.0 | 7.0 | 19.0 | 16.9 | 134 | 75 |
| Day 27 (24 hrs 28% O2) | 0.486 | 0.597 | 26.9 | 6.2 | 20.7 | 15.8 | 161 | 89 |
| Day 28 (24 hrs 39.5% O2) | 0.486 | 0.486 | 28.0 | 8.4 | 19.6 | 16.7 | 204 | 98 |
| Day 29 (48 hrs 39.5% O2) | 0.529 | 0.448 | 39.0 | 12.3 | 26.7 | 13.8 | 236 | 97 |
| Day 30 (24 hrs 52.6% O2) | 0.529 | 0.392 | 39.5 | 13.1 | 26.4 | 12.0 | 246 | 100 |
| Day 31 (48 hrs 52.6% O2) | 0.554 | 0.394 | 52.6 | 20.3 | 32.3 | 10.8 | 267 | 100 |
| Day 32 (24 hrs 78.9% O2) | 0.554 | 0.390 | 52.6 | 20.2 | 32.4 | 10.3 | 322 | 98 |
| Day 33 (48 hrs 78.9% O2) | 0.561 | 0.897 | 78.0 | 47.8 | 30.2 | 15.1 | 295 | 89 |

Example 3

Higher than Atmospheric Partial Pressures of Oxygen and Factor V Production

To further investigate the beneficial effects of higher than atmospheric partial pressures of oxygen in a BAL device, Factor V production was evaluated.

Factor V is used as an indicator of liver function in a clinical setting. Compared to albumin, which has a half life of ~20 days in serum, factor V has a much shorter half life of ~2 hours in serum. Thus, Factor V can be a more sensitive diagnostic indicator of liver health, especially in a liver that is metabolically unstable, such as a failing liver. For example, factor V levels are a component of the international normalized score (INR), which is a standardized measure that reflects partial thrombin, i.e., clotting time. INR, in turn, is a component of Model End Stage Liver Disease (MELD)

secondary antibody conjugated to peroxidase was bound to the primary antibodies and the antibody sandwich was incubated with o-phenylenediamine (OPD) substrate. Factor V concentrations were determined using an ELISA plate reader reading absorbance at ~490 nm of hydrolyzed OPD substrate. Sample absorbance readings were converted to protein quantity using a standardized reference curve constructed using known concentrations of factor V. Reference curve was validated by "back fit" analysis, which indicated a correlation coefficient of 0.962.

Results

The results shown in Table 3 indicate that increasing the oxygen concentration available to ELAD hepatocytes causes a dose-dependent increase in factor V production. The data are consistent with those of Example 2 indicating that BAL hepatocyte health increased under higher than atmospheric partial pressures of oxygen. However, unlike the results observed with ammonia, factor V production continued to increase as oxygen concentrations in the feed line were maintained at 78.9% oxygen for 48 hours.

These results indicate that the oxygen toxicity observed in Example 2, supra, does not necessarily extend to all markers of hepatocyte health. These results also indicate that in some situations it may be desirable to elevate oxygen concentration supplied to BAL hepatocytes beyond 52.6% for a short time. For example, it may be desirable to raise the concentration beyond 52.6% when a patient is in need of increased plasma concentration of a pro-thrombin factor such as factor V, and the benefit of raising the oxygen concentration outweighs the ill effects of reduced ammonia metabolism.

TABLE 3

| $FiO_2$ | factor V μg/total | factor V μg/min | factor V μg/hour |
|---|---|---|---|
| 21% | 875.3 | 5.0 | 300.1 |
| 21% | 912.3 | 5.2 | 312.8 |
| 28% | 1055.1 | 6.0 | 361.7 |
| 39% | 1249.2 | 7.1 | 428.3 |
| 39% | 1168.6 | 6.7 | 400.7 |
| 52.6% | 1175.9 | 6.7 | 403.2 |
| 52.6% | 1121 | 6.4 | 384.3 |
| 78.9% | 1263.8 | 7.2 | 433.3 |
| 78.9% | 1307.7 | 7.5 | 448.4 |

Example 4

Increased Factor V Production is a Durable Result

To test the durability of beneficial effects associated with higher than atmospheric partial pressures of oxygen in a BAL device, Factor V production was evaluated over a longer period of time.

Three ELAD™ cartridges were arranged as described in Example 2. Oxygen to the inlet line was maintained for 26 days at slightly higher than atmospheric partial pressures of oxygen (21-28% FiO2) to bring hepatocytes to a metabolic plateau. After 28 days, the partial pressure of oxygen was raised to 52.6%. Factor V production was measured as described in Example 3. Lower amounts of total factor V measured relative to other results, e.g., in Example 2, may reflect lower intrinsic production rates of this protein relative to other key proteins, fewer total hepatocytes in the system, and/or reduced factor V production over time.

Results

The results of this experiment are shown in Table 4. Generally the data indicate that when partial pressure of oxygen in the inlet line was raised to 52.6%, even after 50 days in culture, BAL hepatocytes continue to produce significant amounts of factor V. Thus, the data indicate that under higher than atmospheric partial pressures of oxygen factor V production is a durable cellular function in BAL hepatocytes.

TABLE 4

| $FiO_2$ | Day | μg/total | μg/min | μg/hour |
|---|---|---|---|---|
| 52.6% | 44 | 315 | 1.4 | 81.00 |
| 52.6% | 45 | 315 | 1.4 | 81.00 |
| 52.6% | 46 | 263 | 1.1 | 67.63 |
| 52.6% | 47 | 315 | 1.4 | 81.00 |
| 52.6% | 48 | 140 | 0.6 | 36.00 |
| 52.6% | 49 | 263 | 1.1 | 67.63 |
| 52.6% | 50 | 228 | 1.0 | 58.63 |
| 52.6% | 51 | 350 | 1.5 | 90.00 |

TABLE 4-continued

| $FiO_2$ | Day | μg/total | μg/min | μg/hour |
|---|---|---|---|---|
| 52.6% | 52 | 210 | 0.9 | 54.00 |
| 52.6% | 53 | 420 | 1.8 | 108.00 |

Example 5

Monitoring and Optimizing BAL Hepatocyte Function

ELAD cartridges are set up as described in Example 2. Levels of the following compounds are monitored individually or in groups: α-1 antichymotrypsin, α-1 anti-trypsin, antithrombin 3, factor VII, and C3 complement. Compound levels are monitored using ELISA assays similar to the one described in Example 3. Since deficiencies of these compounds are associated with poor hepatocyte health, the following tests can be done to show that increasing oxygen concentration improves hepatocyte health in a BAL.

The partial pressure of oxygen is increased in the ELAD inlet line for two days. In one test, oxygen level is raised to 28%. In another test, oxygen level is raised to 39%. In a third test, oxygen level is raised to 52.6%. Increasing the oxygen concentration causes an increase in the amount of α-1 antichymotrypsin, α-1 anti-trypsin, antithrombin 3, factor VII, and/or C3 complement generated by hepatocytes.

In one test, ELAD hepatocytes are grown for 44 days, and then oxygen levels are maintained at 52.6% during days 44-60. During days 44-60, hepatocytes produce significant amounts of α-1 antichymotrypsin, α-1 anti-trypsin, antithrombin 3, factor VII, and/or C3 complement.

Thus, increasing oxygen concentration has a differentially positive, as well as durable impact on a variety of health indicators generated by BAL hepatocytes. For example, different markers measured in the Examples herein, exhibit peak production rates at different inlet oxygen concentrations. Therefore, oxygen concentrations can be varied to achieve different therapeutic effects related to the markers.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An organ support system comprising:
   a hemodialysis recirculation conduit comprising a first end and a second end, and an inlet and an outlet located between the first and second ends; and
   a hemodialysis device comprising a first port and a second port, and configured to produce dialyzed fluid, wherein:
   the first end of the conduit is configured to connect to the first port and the second end of the conduit is configured to connect to the second port;
   a first line carries fluid from a subject to the inlet and a second line carries fluid from the outlet to the subject; and
   the system is configured so that at least a portion of fluid carried from the subject to the recirculation conduit can be dialyzed more than once by the hemodialysis device before being carried by the second line from the recirculation conduit to the subject.

2. The organ support system of claim 1, further comprising:
a bioreactor arranged to receive at least a fraction of the dialyzed fluid from the hemodialysis device to thereby generate a processed fluid, or fraction thereof, that can be subsequently removed by the second line.

3. The organ support system of claim 2, further comprising an ultrafiltrate generator arranged to receive fluid from the hemodialysis device to generate an ultrafiltrate fraction and a concentrated fluid fraction,
wherein the system is configured so that the ultrafiltrate fraction can pass to the bioreactor to generate a processed ultrafiltrate fraction.

4. The organ support system of claim 3, wherein the system is configured so that processed ultrafiltrate fraction can be subsequently recombined with the concentrated fluid fraction to generate a processed whole fluid fraction that can be subsequently removed from the recirculation conduit by the second line.

5. The organ support system of claim 3, wherein the system is configured so that the ultrafiltrate generator receives fluid from the first line to generate an ultrafiltrate fraction that can subsequently pass to the hemodialysis device.

6. The organ support system of claim 3, wherein the system is configured so that the ultrafiltrate generator receives fluid from the hemodialysis device to generate an ultrafiltrate fraction that can be subsequently passed to the bioreactor.

7. The organ support system of claim 2, wherein the bioreactor is a bioartificial liver support bioreactor.

8. The organ support system of claim 1, wherein the hemodialysis machine comprises a continuous venovenous hemofiltration device.

9. The organ support system of claim 1, further comprising:
the first line configured to carry fluid from a subject to the recirculation conduit inlet; and
the second line configured to carry fluid from the recirculation conduit outlet to the subject.

10. A method for enhancing the function of a bioartificial organ support system, the method comprising:
obtaining a subject's blood;
passing at least a fraction of the blood through a hemodialysis device to produce dialyzed blood;
separating the dialyzed blood into a first dialyzed portion and a second dialyzed portion;
recirculating the first dialyzed portion through the hemodialysis device; and
returning the second dialyzed portion to the subject.

11. The method of claim 10 further comprising:
passing at least a fraction of the dialyzed portion through a bioreactor to generate processed blood;
separating the processed blood into a first processed portion and a second processed portion;
recirculating the first processed portion through the hemodialysis device and the bioreactor; and
returning the second processed portion to the subject.

12. The method of claim 11, further comprising:
exposing cells in the bioreactor to a higher than atmospheric concentration of oxygen.

13. The method of claim 12, further comprising:
separating the blood into a concentrated blood fraction and an ultrafiltrate fraction;
adding oxygen to the ultrafiltrate fraction of the blood to achieve a higher than atmospheric concentration of oxygen, thereby producing oxygenated ultrafiltrate;
subsequently processing the oxygenated ultrafiltrate in the bioreactor;
optionally mixing the processed ultrafiltrate with the concentrated blood fraction prior to returning at least a portion of the processed ultrafiltrate, as processed whole blood, to the patient; and
delivering at least a portion of the processed ultrafiltrate to the subject.

14. The method of claim 13, wherein the bioreactor is a bioartificial liver support bioreactor.

15. The method of claim 13, wherein the processed ultrafiltrate is mixed with the concentrated blood fraction to make the processed whole blood and at least a fraction of the processed ultrafiltrate is returned to the patient as a component of the processed whole blood.

16. The method of claim 12, wherein the bioreactor is a bioartificial liver support bioreactor.

17. The method of claim 12, wherein the cells are exposed to the higher than atmospheric concentration of oxygen when the blood or blood fraction is being processed by the bioreactor.

18. The method of claim 12, wherein the higher than atmospheric concentration of oxygen is produced by adding a gas comprising oxygen to the blood or blood fraction introduced to the bioreactor.

19. The method of claim 12, wherein the higher than atmospheric concentration of oxygen is produced by adding a gas comprising oxygen to the bioreactor.

20. The method of claim 12, wherein the higher than atmospheric concentration of oxygen is at least approximately 26% and less than 79%.

21. The method of claim 12, wherein the higher than atmospheric concentration of oxygen is between approximately 26% and approximately 70%.

22. The method of claim 12, wherein the higher than atmospheric concentration of oxygen is approximately 52.6%.

23. The method of claim 11, wherein the bioreactor is a bioartificial liver support bioreactor.

24. The method of claim 10, wherein the organ support system comprises an ultrafiltrate generator, and the method further comprises:
passing the dialyzed blood to the ultrafiltrate generator to generate an ultrafiltrate fraction and a concentrated blood fraction;
processing the ultrafiltrate fraction through a bioreactor to generate processed ultrafiltrate;
subsequently combining the processed ultrafiltrate with the concentrated blood fraction to form processed whole blood;
separating the processed whole blood into a first portion of dialyzed blood and a second portion of dialyzed blood; and
recirculating the first portion of dialyzed blood through the hemodialysis machine and the bioreactor.

25. The method of claim 10, wherein the hemodialysis device is a continuous venovenous hemofiltration device.

26. The method of claim 10, wherein the organ support system has a plurality of flow rates that are in a steady state equilibrium; the first dialyzed portion of blood that is recirculated through the dialysis device has a recirculated flow rate, and the second portion of blood that is returned to the subject has a non-recirculated flow rate, and the method further comprises maintaining or adjusting the flow rates to achieve a ratio of the recirculated flow rate to the non-recirculated flow rate of between 0.1 to 1 and 10 to 1, inclusive.

* * * * *